(12) United States Patent
Fankhauser et al.

(10) Patent No.: US 9,187,710 B2
(45) Date of Patent: Nov. 17, 2015

(54) CYCLODODECADIENOL DERIVATIVES AS PERFUMING INGREDIENTS

(71) Applicant: FIRMENICH SA, Geneva (CH)

(72) Inventors: Peter Fankhauser, Geneva (CH); Olivier Etter, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/372,887

(22) PCT Filed: Jan. 9, 2013

(86) PCT No.: PCT/EP2013/050270
§ 371 (c)(1),
(2) Date: Jul. 17, 2014

(87) PCT Pub. No.: WO2013/107673
PCT Pub. Date: Jul. 25, 2013

(65) Prior Publication Data
US 2014/0378359 A1    Dec. 25, 2014

(30) Foreign Application Priority Data

Jan. 17, 2012  (EP) .................................... 12151381

(51) Int. Cl.
*C11D 3/50* (2006.01)
*C11B 9/00* (2006.01)
*C07C 43/303* (2006.01)

(52) U.S. Cl.
CPC ............. *C11B 9/0038* (2013.01); *C07C 43/303* (2013.01)

(58) Field of Classification Search
CPC ........................... C11B 9/0015; C11B 9/0038
See application file for complete search history.

(56) References Cited

U.S. PATENT DOCUMENTS

| 3,128,304 A | 4/1964 | Lafont et al. |
| 3,184,491 A | 5/1965 | Lafont et al. |
| 3,281,474 A | 10/1966 | Leidig |
| 3,993,697 A | 11/1976 | Bruns et al. |
| 2003/0130163 A1 | 7/2003 | Margot et al. |

FOREIGN PATENT DOCUMENTS

| EP | 116127 A1 | 8/1984 |
| EP | 965575 A1 | 12/1999 |
| GB | 893068 A | 4/1962 |
| SU | 1657483 * | 6/1991 |
| SU | 1657483 A1 | 6/1991 |

OTHER PUBLICATIONS

E. Balbolov et al., Oxidation Communications (2003), vol. 26, issue 2, pp. 193-197. Abstract.*
International Search Report and Written Opinion, application PCT/EP2013/050270, mailed May 7, 2013.
Champalbert et al., Tetrahedron Letters, 1977, 18(37), 3251-3254.
Lombardo et al., Journal of Organic Chemistry (1991), 56, 2422-2427.
Zakharkin et al., Doklady Akademii Nauk SSSR (1961), 138, 373-6.
Zakharkin et al., Izvestiya Akademii Nauk SSSR (1961), 159-60.
Zapesochnaya et al., Zhurnal Obshchei Khimii (1963), 33(7), 2133-6.

* cited by examiner

*Primary Examiner* — John Hardee
(74) *Attorney, Agent, or Firm* — Winston & Strawn LLP

(57) ABSTRACT

The present invention relates to a composition of matter comprising at least 95% w/w of at least one compound of formula (I), wherein R group is a $C_{1-6}$ alkyl group optionally comprising an ether functional group; and wherein each carbon-carbon double bond of said compound, independently from each other, can be in a configuration Z or E; which is a useful perfuming ingredient.

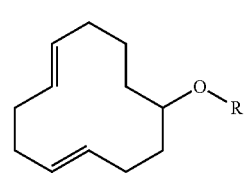

(I)

9 Claims, No Drawings

CYCLODODECADIENOL DERIVATIVES AS PERFUMING INGREDIENTS

TECHNICAL FIELD

The present invention relates to the field of perfumery. More particularly, it concerns the use as perfuming ingredient of a composition of matter comprising at least 95% w/w of at least one compound of formula (I) as defined below. The present invention also comprises the compositions wherein the invention's composition of matter is part of a perfuming composition or of a perfuming consumer product.

PRIOR ART

To the best of our knowledge, in general terms ethers and acetals of cyclododecadienol derivatives according to the invention are unknown products with the exception of 9-ethoxy-1,5-cyclododecadiene and 9-methoxy-1,5-cyclododecadiene which are disclosed, in SU 1657483 (Accession Number 1992:447990) and in U.S. Pat. No. 3,184,491, as chemical intermediates. None of the prior art discloses or suggests the use of the invention's composition of matter as perfuming ingredients.

The perfumery industry uses or knows several derivatives of cyclododecanol as perfuming ingredients (e.g. (1-ethoxyethoxy)cyclododecane described in US 2003/0130163; (methoxymethoxy)cyclododecane described in U.S. Pat. No. 3,993,697; or also the ethers of cyclododecanol described in U.S. Pat. No. 3,281,474, but all possess a significantly different skeleton (i.e. the cycle is totally saturated). The closest known analogues of the invention's composition of matter are 5,9-cyclododecadien-1-ol (see U.S. Pat. No. 3,128,304) but once again these compounds are significantly different (an alcohol versus an ether or acetal) and have different odors as discussed below. Further below in Table 1 are highlighted the differences between the invention's composition of matter and the prior art compounds.

These prior art documents do not report or suggest any organoleptic properties of the compounds of formula (I), and do not report or suggest any use of said compounds in the field of perfumery.

DESCRIPTION OF THE INVENTION

We have now surprisingly discovered that a cyclododecadienol ether or acetal in the form of a composition of matter comprising at least 95% w/w of at least one compound of formula

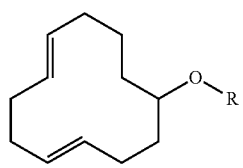

(I)

wherein R is a $C_{1-6}$ alkyl group optionally comprising an ether functional group; and
wherein each carbon-carbon double bond of said compound, independently from each other, can be in a configuration Z or E;

can be used as perfuming ingredient, for instance to impart odor notes of the woody/amber type with connotation of the alliaceous, balsamic and/or green type.

According to any one of the above embodiments of the invention, R is a $C_{1-4}$, or even a $C_{3-4}$, alkyl group or a $C_{3-5}$ group of formula $CR'_2OCHR'_2$, each R' representing independently from each other a hydrogen atom or a methyl group.

According to any one of the above embodiments of the invention, R is a $C_{3-4}$ group of formula $CHR'OCHR'_2$, each R' representing independently from each other a hydrogen atom or a methyl group.

According to any one of the above embodiments of the invention, R is a $C_{3-4}$ group of formula $CHR'OCH_2R'$, and one R' presenting a methyl group and the other representing a hydrogen atom or a methyl group.

For the sake of clarity, by the expression "each carbon-carbon double bond of said compound, independently from each other, can be in a configuration Z or E" it is meant the normal meaning in the art, i.e. that said composition of matter can be in the form of an essentially pure stereoisomer (i.e. the (1E,5Z), (1Z,5E) or (1E,5E) isomer) or in the form of a mixture of stereoisomers, e.g. in a mixture comprising the stereoisomers (1E,5E), (1Z,5E) and (1E,5Z) in various w/w ratio.

According to any one of the above embodiments of the invention, the invention's composition of matter can be in the form of a mixture containing predominantly the stereoisomers (1E,5E), (1Z,5E) or/and (1E,5Z), the remaining being essentially the (1Z,5Z) stereoisomer. In such a case, one may define a w/w ratio (1E,5E)/[(1Z,5E)+(1E,5Z)] for such mixture of stereoisomers (also referred to as the (E,E)/(E,Z) ratio). According to a particular aspect of said embodiment, the composition of matter is in the form of a mixture of stereoisomers having a (E,E)/(E,Z) ratio comprised between 20/80 and 1/99. According to said embodiment, said a mixture of stereisomers has a (E,E)/((E,Z) ratio comprised between 8/92 and 3/97.

Alternatively said composition of matter is in the form of a mixture of stereoisomers having a (E,E)/((E,Z) ratio comprised between 80/20 and 99.5/0.5. According to said embodiment, said mixture of stereoisomers has a (E,E)/((E,Z) ratio comprised between 90/10 and 99/1.

For the sake of clarity, by the expression "predominantly" it is meant that the mentioned stereoisomers or mixture of stereoisomers represent more than 90% or even more than 94% of said composition of matter, the remaining being obviously in the form of the other isomers.

As specific examples of the invention's composition of matter, one may cite, as non-limiting example, (1E,5E)-9-(1-ethoxyethoxy)cyclododeca-1,5-diene (i.e. a 9-(1-ethoxyethoxy)cyclododeca-1,5-diene in the form of a (E,E)/(E,Z) mixture 99/1 w/w, and also herein after referred to as "compound 1"). Said compound 1 possesses a unique odor having a woody/amber character with clear alliaceous/garlic and balsamic/incense notes. The overall odor reminds somehow of the odor of 8,13:13,20-diepoxy-15,16-dinorlabdane. The odor of the invention's composition of matter does have also a cosmetic connotation due to some velvety, methylionone, raspberry type of softness.

As other specific, but non-limiting, examples of the invention's composition of matter, one may cite the following ones in Table 1:

TABLE 1

Invention's compositions of matter and their odor properties and prior art compounds

| Compound structure and name | Odor notes |
|---|---|
| 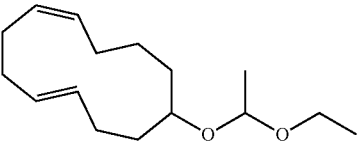<br><br>(1Z,5E)-9-(1-ethoxyethoxy)cyclododeca-1,5-diene/<br>(1E,5Z)-9-(1-ethoxyethoxy)cyclododeca-1,5-diene<br>(i.e. a 9-(1-ethoxyethoxy)cyclododeca-1,5-diene in the form of a (E,E)/(E,Z) mixture 5/95 w/w, and also herein after referred to as "compound 2") | Odor having a woody/amber character with clear green, alliaceous/garlic and balsamic/myrrh/opoponax notes. |
| 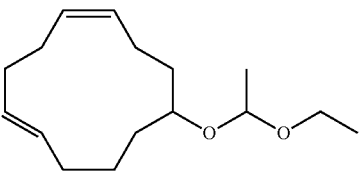<br><br>(1E,5Z)-9-(1-ethoxyethoxy)cyclododeca-1,5-diene<br>(i.e. a 9-(1-ethoxyethoxy)cyclododeca-1,5-diene in the form of a pure stereoisomer with 96% purity, and also herein after referred to as "compound 3") | Odor having a woody/amber character with balsamic note. |
| 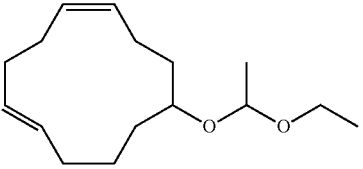<br><br>(1Z,5E)-9-(1-ethoxyethoxy)cyclododeca-1,5-diene<br>(i.e. a 9-(1-ethoxyethoxy)cyclododeca-1,5-diene in the form of a pure stereoisomer with a 98% purity, and also herein after referred to as "compound 4") | Odor having a woody/amber character with fruity and balsamic/vanilla notes. |
| 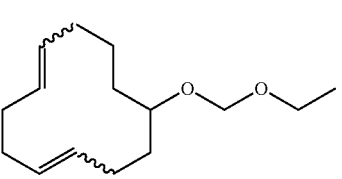<br><br>9-(ethoxyethoxy)-1,5-cyclododecadiene<br>(i.e. a 9-(ethoxymethoxy)-1,5-cyclododecadiene in the form of a (E,E)/(E,Z) mixture 5/95 w/w, and also herein after referred to as "compound 5"). | Odor having a woody/amber character with a clear green, pineapple type, note as well as a nutty aspect. |

Prior art compounds

| | |
|---|---|
| 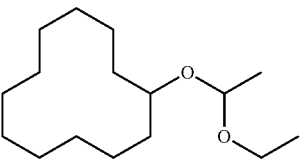<br><br>(1-ethoxyethoxy)cyclododecane | Weak woody note, essentially acting as fixative or enhancer of other ingredients. No alliaceous, balsamic and/or green notes. |

TABLE 1-continued

Invention's compositions of matter and their odor properties and prior art compounds

| Compound structure and name | Odor notes |
|---|---|
| 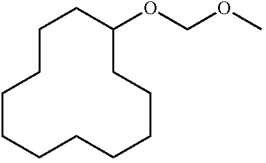<br>(methoxymethoxy)cyclododecane | Typically woody, ambery odor. No alliaceous, balsamic and/or green notes. |
| the ethers of cyclododecanol described in U.S. Pat. No. 3,281,474 | Cedar, like odors. No alliaceous, balsamic and/or green notes. |
| 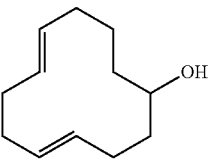<br>5,9-cyclododecadien-1-ol (see U.S. Pat. No. 3,128,304) | Natural amber. No alliaceous, balsamic and/or green notes. |

According to a particular embodiment of the invention, the composition of matter is (1E,5Z)-9-(1-ethoxyethoxy)cyclododeca-1,5-diene or 9-(1-ethoxyethoxy)cyclododeca-1,5-diene in the form of a mixture containing predominantly any one of the stereoisomers (1E,5E), (1Z,5E) or/and (1E,5Z).

When the odor of the invention's composition of matter is compared with that of the prior art compounds, then the invention's composition of matter distinguishes itself by having alliaceous, balsamic and/or green notes. Said differences lend the invention's composition of matter and the prior art compounds to be each suitable for different uses, i.e. to impart different organoleptic impressions.

The composition of matter of the invention wherein
R is a $C_{3-4}$ alkyl group or a $C_{1-4}$ group of formula CHR'OCHR'$_2$, each R' representing independently from each other a hydrogen atom or a methyl group; and in particular R is a group of formula CHR'OCH$_2$R', and one R' presenting a methyl group and the other representing a hydrogen atom or a methyl group; and
said composition being in the form of any one of its stereoisomers or a mixture thereof;
is a novel composition and therefore also an object of the present invention.

As mentioned above, the invention concerns the use of the invention's composition of matter as perfuming ingredient. In other words, it concerns a method to confer, enhance, improve or modify the odor properties of a perfuming composition or of a perfumed article, which method comprises adding to said composition or article an effective amount of the composition of matter. By "use of composition of matter" it has to be understood here also the use of any composition containing composition of matter and which can be advantageously employed in the perfumery industry.

Said compositions, which in fact can be advantageously employed as perfuming ingredients, are also an object of the present invention.

Therefore, another object of the present invention is a perfuming composition comprising:

i) as perfuming ingredient, the invention's composition of matter as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. which does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Geliermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of the invention's composition of matter and at least one perfumery carrier represents a particular embodiment of the invention as well as a perfuming composition comprising the invention's composition of matter, at least one perfumery carrier, at least one perfumery base, and optionally at least one perfumery adjuvant.

It is useful to mention here that the possibility to have, in the compositions mentioned above, more than one composition of matter is important as it enables the perfumer to prepare accords, perfumes, possessing the odor tonality of various compositions of matter of the invention, creating thus new tools for his work.

For the sake of clarity, it is also understood that any mixture resulting directly from a chemical synthesis, e.g. a reaction medium without an adequate purification, in which the composition of matter of the invention would be involved as a starting, intermediate or end-product could not be considered as a perfuming composition according to the invention as far as said mixture does not provide the inventive composition of matter in a suitable form for perfumery. Thus, unpurified reaction mixtures are generally excluded from the present invention unless otherwise specified.

Furthermore, the invention's composition of matter can also be advantageously used in all the fields of modern perfumery, i.e. fine or functional perfumery, to positively impart or modify the odor of a consumer product into which said composition of matter is added. Consequently, a perfuming consumer product which comprises:

i) as perfuming ingredient, the invention's composition of matter, as defined above; and
ii) a perfumery consumer base;

is also an object of the present invention.

The invention's composition of matter can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's composition of matter.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's composition of matter, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the composition of matter according to the invention can be incorporated into the various aforementioned articles or compositions vary within a wide range of values. These values are dependent on the nature of the article to be perfumed and on the desired organoleptic effect as well as the nature of the co-ingredients in a given base when the composition of matter according to the invention are mixed with perfuming co-ingredients, solvents or additives commonly used in the art.

For example, in the case of perfuming compositions, typical concentrations are in the order of 1% to 40% by weight, or even more, of the invention's composition of matter of the invention based on the weight of the composition into which they are incorporated. Concentrations lower than these, such as in the order of 0.1% to 10% by weight, can be used when said the invention's compositions of matter are incorporated into perfumed articles, percentage being relative to the weight of the article.

The invention's compositions of matter can be prepared according to the literature for the ketone or standard methods known in the art as described herein below.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Starting cyclododecadienols were prepared according to the literature.

E,E-4,8-Cyclododecadiene-1-ol: CAS RN: 55147-54-1
  a) Zakharkin, L. I.; Korneva, V. V.; Iogansen, A. V.; Doklady Akademii Nauk SSSR (1961), 138, 373-6.
  b) Zakharkin, L. I.; Korneva, V. V.; Izvestiya Akademii Nauk SSSR, Seriya Khimicheskaya (1961), 159-60.
  c) Zapesochnaya, G. G.; Kovtun, I. A.; Sarycheva, I. K.; Preobrazhenskii, N. A.; Zhurnal Obshchei Khimii (1963), 33 (7), 2133-6.
  d) GB 893068 19620404 (1962).

E,Z-4,8-Cyclododecadien-1-ol: CAS RN: 65763-11-3
  Champalbert, J.; Guillois, A.; Jullien, J.; Jullien, R.; Nguyen Thoi Lai; Pascard, C.; Prange, T.; Tetrahedron Letters (1977), (37), 3251-4.

Z,E-4,8-Cyclododecadien-1-ol: CAS RN: 65763-10-2
  a) Lombardo, Franco; Newmark, Richard A.; Kariv-Miller, Essie; Journal of Organic Chemistry (1991), 56 (7), 2422-7.
  b) Champalbert, J.; Guillois, A.; Jullien, J.; Jullien, R.; Nguyen Thoi Lai; Pascard, C.; Prange, T.; Tetrahedron Letters (1977), (37), 3251-4.

The compounds cyclododecadienols can be admixed together to obtain different blends of the various isomers.

Example 1

Synthesis of Composition of Matter
  (1E,5E)-9-(1-ethoxyethoxy)cyclododeca-1,5-diene (Compound 1)

To a mechanically stirred mixture of E,E-4,8-cyclododecadien-1-ol (99% (E,E)/1% (E/Z), 2.0 g, 11 mmol), toluene sulphonic acid monohydrate (0.15 g, 2 mmol) and MTBE (methyl terbutyl ether, 20 mL) was added drop wise ethyl vinyl ether (5 g) over 15 minutes. The reaction mixture was heated at reflux at 40° C. for 1 hour, then diluted with MTBE, washed with aqueous NaHCO$_3$, water and brine. The solvent was evaporated and the product (4.5 g) purified by flash distillation (Kugelrohr, 86° C., 0.1 mbar) and liquid chromatography (silica gel 100 g; eluent=heptane/ethyl acetate 95/5).

The fractions containing the target mixed acetal were pooled and concentrated to give 1.7 g (yield 44%; 55/45 diastereomer mixture) as a colorless oil.

Spectral data for a 55/45 mixture of the two diastereo isomers:

$^{13}$C NMR: 15.4 (q), 15.5 (q), 20.7 (q), 21.0 (q), 22.8 (t), 22.9 (t), 29.4 (t), 29.5 (t), 29.6 (t), 29.7 (t), 30.2 (t), 30.7 (t), 32.1 (t), 32.1 (t), 32.2 (t), 32.2 (t), 32.3 (t), 33.8 (t), 59.6 (t), 59.9 (t), 72.6 (d), 75.0 (d), 97.5 (d), 100.3 (d), 130.4 (d), 130.6 (d), 131.1 (d), 131.4 (d), 131.8 (d), 131.9 (d), 132.1 (d), 132.1 (d).

$^1$H—NMR: 1.15-1.25 (m, 3H); 1.30-1.35 (m, 3H); 1.38-21.90 (m, 4H); 1.95-2.25 (m, 8H); 3.42-3.67 (m, 3H); 4.70-4.78 (m, 1H); 5.04-5.26 (m, 4H).

9-(1-Ethoxyethoxy)cyclododeca-1,5-diene (E,Z/Z,E mixture) (Compound 2)

Reacting 4,8-cyclododecadien-1-ol (in the form of a 47% E,Z-, 48% Z,E- and 5% E,E isomer mixture) with ethyl vinyl ether using the same procedure as above yielded the target mixed acetals. An isomeric mixture (isomer ratio 29/29/21/21 by GC) was obtained.

Selected spectral data for the mixture of the four main components:

$^{13}$C NMR: 60.0 (t), 60.1 (t), 60.2 (t), 60.4 (t), 71.8 (d), 72.3 (d), 74.3 (d), 74.5 (d).

$^1$H—NMR: 1.18-1.24 (m, 4H); 1.27-1.33 (m, 3H); 1.34-1.52 (m, 2H); 1.53-2.30 (m, 11H); 3.48-3.76 (m, 3H); 4.65-4.78 (m, 1H); 5.08-5.26 (m, 1H); 5.08-5.48 (m, 3H).

(1E-5Z)-9-(1-Ethoxyethoxy)cyclododeca-1,5-diene (Compound 3)

Reacting (4Z-8E)-cyclododecadien-1-ol with ethyl vinyl ether using the same procedure as above yielded the target mixed acetals as a diastereomeric mixture.

$^{13}$C NMR: 15.4 (q), 15.5 (q), 20.8 (q), 21.0 (q), 21.4 (t), 21.4 (t), 23.8 (t), 23.9 (t), 28.8 (t), 30.0 (t), 30.3 (t), 30.5 (t), 30.5 (t), 31.2 (t), 31.3 (t), 34.0 (t), 35.3 (t), 60.2 (t), 60.4 (t), 72.3 (d), 74.3 (d), 97.5 (d), 100.2 (d), 128.8 (d), 128.9 (d), 129.2 (d), 129.5 (d), 131.3 (d), 131.4 (d), 132.4 (d), 132.5 (d); 1.52-1.85 (m, 3H).

$^1$H—NMR: 1.17-1.24 (m, 3H); 1.28-1.33 (m, 3H); 1.33-1.52 (m, 2H); 1.52-1.85 (m, 3H); 1.85-2.25 (m, 9H); 3.38-3.70 (m, 3H); 4.65-4.75 (m, 1H); 5.12-5.23 (m, 1H). 5.28-5.45 (m, 3H).

(1Z-5E)-9-(1-Ethoxyethoxy)cyclododeca-1,5-diene (Compound 4)

Reacting (4E-8Z)-cyclododecadien-1-ol with ethyl vinyl ether using the same procedure as above yielded the target mixed acetals as a diastereomeric mixture.

$^{13}$C NMR: 15.4 (q), 15.5 (q), 20.7 (q), 21.0 (q), 23.5 (t), 23.5 (t), 28.8 (t), 28.9 (t), 29.5 (t), 29.7 (t), 30.9 (t), 31.1 (t), 31.2 (t), 32.5 (t), 60.0 (t), 60.1 (t), 71.8 (d), 74.5 (d), 97.5 (d), 100.5 (d), 128.2 (d), 128.4 (d), 128.8 (d), 128.9 (d), 131.9 (d), 132.0 (d), 132.3 (d), 132.4 (d).

$^1$H-NMR: 1.19-1.24 (t, 3H); 1.28-1.33 (t, 3H); 1.35-1.48 (m, 2H); 1.55-178 (m, 2H); 1.78-2.34 (m, 10H); 3.48-3.84 (m, 3H); 4.64-4.78 (m, 1H); 5.13-5.48 (m, 4H).

9-(Ethoxymethoxy)-1,5-cyclododecadiene (E,Z/E,E Mixture) (Compound 5)

To a mechanically stirred mixture of 4,8-cyclododecadien-1-ol (5.4 g, 30 mmol; in the form of a 47% E,Z-, 48% Z,E- and 5% E,E isomer mixture), formaldehyde diethyl acetal (31.2 g, 294 mmol) and lithium bromide (0.52 g, 6 mmol) was added toluene sulphonic acid monohydrate (0.57 g, 3 mmol). The mixture was stirred at room temperature for 3 hours, then diluted with MTBE, washed with aqueous NaHCO3, water and brine. The solvent was evaporated and the product purified by liquid chromatography (silica gel 230 g; eluent=heptane/ethyl acetate 95/5).

The fractions containing the target mixed acetals were pooled, concentrated and flash distilled (Kugelrohr, 86° C., 0.2 mbar) to give 4.21 g (yield 59%) of an isomer mixture (ratio=48% E,Z; 48% Z,E, 4% E,E) as a colorless oil.

Spectral data for a 1:1 mixture of the two main components:

$^{13}$C NMR: 15.1 (q), 21.5 (t), 23.5 (t), 23.9 (t), 28.7 (t), 28.8 (t), 29.5 (t), 29.9 (t), 30.3 (t), 31.0 (t), 31.3 (t), 31.2 (t), 34.3 (t), 63.2 (t), 63.3 (t), 73.9 (d), 74.2 (d), 93.5 (t), 94.0 (t), 128.3 (d), 128.9 (d), 129.0 (d), 129.2 (d), 131.3 (d), 131.8 (d), 132.3 (d), 132.6 (d).

$^{1}$H—NMR: 1.15-1.25 (m, 4H); 1.25-1.50 (m, 2H); 1.58-1.68 (m, 1H); 1.71-2.30 (m, 10H); 3.50-3.75 (m, 3H); 4.60-4.66 (q, 1H); 4.72-4.78 (t, 1H); 5.08-5.48 (m, 4H).

EXAMPLE 2

Preparation of a Perfuming Composition

A perfuming composition for shower gel was prepared by admixing the following ingredients:

| Parts by weight | Ingredient |
|---|---|
| 4 | Carbinol acetate |
| 22 | Geranyl acetate |
| 10 | 10%* Pipol acetate |
| 40 | Hexylcinnamic aldehyde |
| 5 | 10%* Ethyl 2-methyl-pentanoate |
| 5 | Gamma undecalactone |
| 5 | 4-(4-Hydroxy-1-phenyl)-2-butanone |
| 15 | Citronellol |
| 3 | 1,1-Dimethyl-2-phenylethyl butanoate |
| 10 | 10%* Damascenone |
| 150 | Dipropylene glycol |
| 185 | 4-(1,1-dimethylethyl)-1-cyclohexyl acetate |
| 5 | Ethylvanilline |
| 50 | Habanolide ®[1] |
| 25 | 3-(1,3-benzodioxol-5-yl)-2-methylpropanal |
| 10 | 10%* Allyl heptanoate |
| 3 | 10%* Indol |
| 3 | 2-Phenoxyethyl isobutyrate |
| 10 | 10%* Isoeugenol |
| 40 | 70%* Methyl gamma ionone |
| 35 | Linalool |
| 150 | Hedione ®[2] |
| 2 | 10%* (E)-8-Decen-5-olide |
| 25 | Hexyl salicylate |
| 100 | Benzyl salicylate |
| 3 | Violet essential oil |
| 50 | Bergamot essential oil |
| 10 | Cassis base[3] |
| 20 | Lemon essential oil |
| 3 | Geranium essential oil |
| 2 | Mandarin essential oil |
| 1000 | |

*in dipropyleneglycol
[1]Pentadecenolide; origin: Firmenich SA, Geneva, Switzerland
[2]Methyl dihydrojasmonate; origin: Firmenich SA, Geneva, Switzerland
[3]Compounded perfumery base; origin: Firmenich SA, Geneva, Switzerland The addition of 150 parts by weight of compound 1 to the above-described composition imparted to the latter a strong woody, amber aspect, and a slightly balsamic note and provided also a cosmetic aspect by the creamy, violet, with a hint of raspberry, softness. The addition of 150 parts by weight of compound 2 to the above-described composition imparted to the latter a strong woody, amber aspect and the fragrance acquired also a resinous, myrrh aspect.

The addition of 150 parts by weight of compound 5 to the above-described composition imparted to the latter a strong woody, amber aspect and the fragrance acquired a green violet leaf, green pineapple aspect as well as an interesting walnut effect.

The addition of 150 parts by weight of (1-ethoxyethoxy)cyclododecane or (methoxymethoxy)cyclododecane enhanced/imparted only the woody/amber aspect of the original composition. No cosmetic, green, balsamic or nutty effects/notes were imparted.

EXAMPLE 3

Preparation of a Perfuming Composition

A perfuming composition for an eau de Cologne was prepared by admixing the following ingredients:

| Parts by weight | Ingredient |
|---|---|
| 10 | Allyl amyl glycolate |
| 30 | Ambrox ®[1] |
| 75 | Bergamote essential oil |
| 60 | Coranol ™[2] |
| 10 | Coumarine |
| 100 | Dihydromyrcenol |
| 5 | 1%* Dorinone ®[3] Beta |
| 50 | Habanolide ®[4] |
| 10 | 1%* Indol |
| 90 | Iso E ®[5] super |
| 5 | Lilyflore ®[6] |
| 50 | Lyral ®[7] |
| 55 | Methyl gamma ionone |
| 5 | Crystal moss |
| 60 | Hedione ®[8] |
| 14 | 10%* (Z)-1-[(E)-2-butenyloxy]-3-hexene |
| 100 | Romandolide ®[9] |
| 10 | 10%* Styrax essential oil |
| 8 | Violet essential oil |
| 3 | 10%* 2,4-Dimethyl-3-cyclohexene-1-carbaldehyde |
| 750 | |

*in dipropyleneglycol
[1](−)-(8R)-8,12-Epoxy-13,14,15,16-tetranorlabdane; origin: Firmenich SA, Geneva, Switzerland
[2]4-Cyclohexyl-2-methyl-2-butanol; origin: Firmenich SA, Geneva, Switzerland
[3]1-(2,6,6-Trimethyl-1-cyclohexen-1-yl)-2-buten-1-one; origin: Firmenich SA, Geneva, Switzerland
[4]Pentadecenolide; origin: Firmenich SA, Geneva, Switzerland
[5]1-(Octahydro-2,3,8,8-tetramethyl-2-naphtalenyl)-1-ethanone; origin: Firmenich SA, Geneva, Switzerland
[6](2,5-Dimethyl-2,3-dihydro-1H-inden-2-yl)methanol; origin: Firmenich SA, Geneva, Switzerland
[7]4/3-(4-Hydroxy-4-methylpentyl)-3-cyclohexene-1-carbaldehyde; origin: International Flavors & Fragrances, USA
[8]Methyl dihydrojasmonate; origin: Firmenich SA, Geneva, Switzerland
[9](1S,1′R)-[1-(3′,3′-Dimethyl-1′-cyclohexyl)ethoxycarbonyl]methyl propanoate; origin: Firmenich SA, Geneva, Switzerland The addition of 250 parts by weight of compound 1 to the above-described composition imparted to the latter an intense woody, amber aspect. The fragrance became more caring and cosmetic by reinforcing the (Methyl)ionones notes and acquired also a new incense aspect.

The addition of 250 parts by weight of compound 2 to the above-described composition imparted to the latter a strong and fresh woody, amber aspect as well as a balsamic aspect of myrrh, opoponax and Vanilla type.

The addition of 250 parts by weight of compound 5 to the above-described composition imparted to the latter a strong woody, amber aspect and the fragrance acquired a nutty to aspect while pushing the green violet leaf, green pineapple aspect of the original fragrance.

The addition of 250 parts by weight of (1-ethoxyethoxy)cyclododecane or (methoxymethoxy)cyclododecane enhanced/imparted only the woody/amber aspect of the original composition. No cosmetic, green, balsamic or nutty effects/notes were imparted.

What is claimed is:

1. A method to confer, enhance, improve or modify the odor properties of a perfuming composition or of a perfumed article, which method comprises adding to said composition or article an effective amount of a composition of matter comprising at least 95% w/w of at least one compound of formula

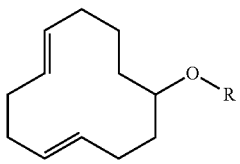

(I)

wherein R group is a $C_{1-6}$ alkyl group optionally comprising an ether functional group; and wherein each carbon-carbon double bond of said compound, independently from each other, can be in a configuration Z or E.

2. The method according to claim 1, wherein said R is a $C_{1-4}$ group or a $C_{3-5}$ group of formula $CR'_2OCHR'_2$, each R' representing independently from each other a hydrogen atom or a methyl group.

3. The method according to claim 1, wherein said composition of matter is in the form of a mixture of stereoisomers of compound (I) having a (E,E)/((E,Z) ratio comprised between 80/20 and 99.5/0.5 or between 8/92 and 3/97.

4. The method according to claim 1, wherein said compound (I) is (1E,5Z)-9-(1-ethoxyethoxy)cyclododeca-1,5-diene or 9-(1-ethoxyethoxy)cyclododeca-1,5-diene in the form of a mixture containing predominantly any one of the stereoisomers (1E,5E), (1Z,5E) or/and (1E,5Z).

5. A composition of matter comprising at least 95% w/w of at least one compound of formula

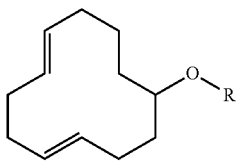

(I)

wherein R is a $C_{3-4}$ alkyl group or a $C_{1-5}$ group of formula $CR'_2OCHR'_2$, each R' representing independently from each other a hydrogen atom or a methyl group; and each carbon-carbon double bond of said compound, independently from each other, can be in a configuration Z or E.

6. A perfuming composition comprising
i) a composition of matter comprising at least 95% w/w of at least one compound of formula

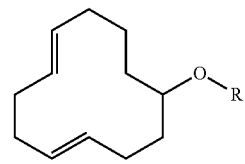

(I)

wherein R group is a $C_{1-6}$ alkyl group optionally comprising an ether functional group; and wherein each carbon-carbon double bond of said compound, independently from each other, can be in a configuration Z or E;
  ii) at least one ingredient selected from the group consisting of a perfumery carrier and a perfumery base; and
  iii) optionally at least one perfumery adjuvant.

7. A perfuming consumer product comprising:
i) a composition of matter comprising at least 95% w/w of at least one compound of formula

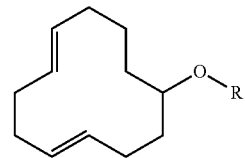

(I)

wherein R group is a $C_{1-6}$ alkyl group optionally comprising an ether functional group; and wherein each carbon-carbon double bond of said compound, independently from each other, can be in a configuration Z or E; and
  ii) a perfumery consumer base.

8. A perfuming consumer product according to claim 7, wherein the perfumery consumer base is a perfume, a fabric care product, a body-care product, an air care product or a home care product.

9. A perfuming consumer product according to claim 7, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *